(12) United States Patent
Lacey

(10) Patent No.: US 7,489,516 B2
(45) Date of Patent: Feb. 10, 2009

(54) DIGITAL CT DETECTOR MODULE METHODS AND APPARATUS

(75) Inventor: Joseph James Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 508 days.

(21) Appl. No.: 11/284,551

(22) Filed: Nov. 22, 2005

(65) Prior Publication Data

US 2006/0110956 A1  May 25, 2006

Related U.S. Application Data

(60) Provisional application No. 60/630,797, filed on Nov. 24, 2004.

(51) Int. Cl.
*H05K 7/14* (2006.01)

(52) U.S. Cl. .............. 361/759; 361/747; 361/818; 361/800; 361/816; 361/740; 378/19; 250/370.08; 250/370.09

(58) Field of Classification Search .............. 361/753, 361/800, 818, 756, 730, 726, 732, 740, 747, 361/759; 378/19; 250/370.09, 370.08
See application file for complete search history.

(56) References Cited

U.S. PATENT DOCUMENTS

| | | | | |
|---|---|---|---|---|
| 4,283,817 A * | 8/1981 | Cotic | ............ | 445/35 |
| 4,414,473 A * | 11/1983 | Hoffman et al. | ....... | 250/370.09 |
| 4,429,227 A * | 1/1984 | DiBianca et al. | ....... | 250/370.09 |
| 5,444,752 A | 8/1995 | Dobbs et al. | | |
| 6,157,696 A | 12/2000 | Saito et al. | | |
| 6,215,843 B1 | 4/2001 | Saito et al. | | |
| 6,249,563 B1 | 6/2001 | Snyder et al. | | |
| 6,292,529 B1 | 9/2001 | Marcovici et al. | | |
| 6,420,711 B2 | 7/2002 | Tumer | | |
| 6,459,727 B1 * | 10/2002 | Cho et al. | ............ | 375/222 |
| 6,459,757 B1 | 10/2002 | Lacey | | |
| 6,535,571 B2 | 3/2003 | Von Der Haar | | |
| 6,658,082 B2 | 12/2003 | Okumura | | |
| 6,667,482 B2 | 12/2003 | Von Der Haar | | |
| 6,883,963 B2 | 4/2005 | Nolewaika et al. | | |
| 6,925,142 B2 * | 8/2005 | Pohan et al. | ............ | 378/19 |
| 6,931,092 B2 | 8/2005 | Joshi et al. | | |
| 6,934,160 B2 | 8/2005 | Heismann et al. | | |
| 6,982,423 B2 * | 1/2006 | Elgali | ............ | 250/370.11 |
| 2004/0065465 A1 | 4/2004 | Chappo et al. | | |

* cited by examiner

*Primary Examiner*—Jeremy C Norris
*Assistant Examiner*—Dameon E Levi
(74) *Attorney, Agent, or Firm*—Armstrong Teasdale LLP

(57) ABSTRACT

A method of installing an electronic board is provided. The method includes inserting the board into a guide in a first direction. The board is then translated in a second direction different from the first direction. Upon inserting the board a gasket is sealed to prevent light, dust, or electromagnetic interference from passing through the gasket. A lock is then engaged to maintain the electronic board in a substantially fixed position.

14 Claims, 16 Drawing Sheets

DIGITAL CT DETECTOR MODULE METHODS AND APPARATUS

CROSS REFERENCE TO RELATED PATENTS

This application claims the benefit of U.S. provisional application No. 60/630,797 filed Nov. 24, 2004, which is herein incorporated in its entirety.

BACKGROUND OF THE INVENTION

This invention relates generally to methods and apparatus for computed tomography (CT), and more particularly to methods and apparatus that provide for a field replaceable CT digital module.

Modular radiation detector arrays typically include a collimator, a scintillator array or package, and a photo diode assembly. The collimator, scintillator package "pack", and diode assembly are precision aligned and attached together to form a detector module. A number of modules are mounted on rails to form the detector array, and pins are fabricated in the pack to enable precise positioning of the pack onto the rails.

The accurate positioning of the collimator, scintillator package, and diode assembly to attach and optically couple them together can be problematic. Additionally, the accurate positioning of the modules relative to one another to form the detector array can be problematic. Because of the X-ray to light conversion process, it is useful that the analog area of a CT module be sealed against all light sources. Further, in order to allow installation and removal of the digital module, a card guide is required to properly align the module for installation and extraction for a CT system. Moreover, the analog portion of the module is subject to Electromagnetic interference (EMI) and requires EMI protection.

One problem with installing a digital module is that the analog module with a pin-in-pack alignment feature is typically moved in the detector Z direction, such that the analog module does not make contact with the collimator rails, before aligning the pin in pack. The digital module is then typically moved in the detector Y direction to bring the analog module into position so that the pin in pack feature engages the collimator combs without damaging a collimator plate. This complex motion has traditionally precluded replacement of modules in the field. The current practice is to use non-field serviceable analog detector modules that, on occasion, experience a failure in the field. When such failure occurs, the entire detector is removed from the CT system, returned to the factory for disassembly and repair. This current practice is costly and time-consuming.

BRIEF DESCRIPTION OF THE INVENTION

In one aspect, a method of installing an electronic board is provided. The method includes inserting the board into a guide in a first direction. The board is then translated in a second direction different from the first direction. Upon inserting the board a gasket is sealed to prevent light, dust, or electromagnetic interference from passing through the gasket. A lock is then engaged to maintain the electronic board in a substantially fixed position.

In another aspect, an electronic board assembly is provided. The assembly includes a guide configured to receive the electronic board in both a first and second direction. A gasket is provided to prevent the passing of light, dust, or electromagnetic interference when the electronic board is inserted into the guide. The assembly further includes a lock to maintain the electronic board in a substantially fixed position after insertion into the guide.

In a further aspect, a medical system is provided. The medical system includes a guide and an electronic board configured to be inserted into the guide. A gasket is provided to prevent the passing of light, dust, or electromagnetic interference when the electronic board is inserted into the guide. The assembly further includes a lock to maintain the electronic board in a substantially fixed position after insertion into the guide.

DETAILED DESCRIPTION OF THE INVENTION

Figure 1:
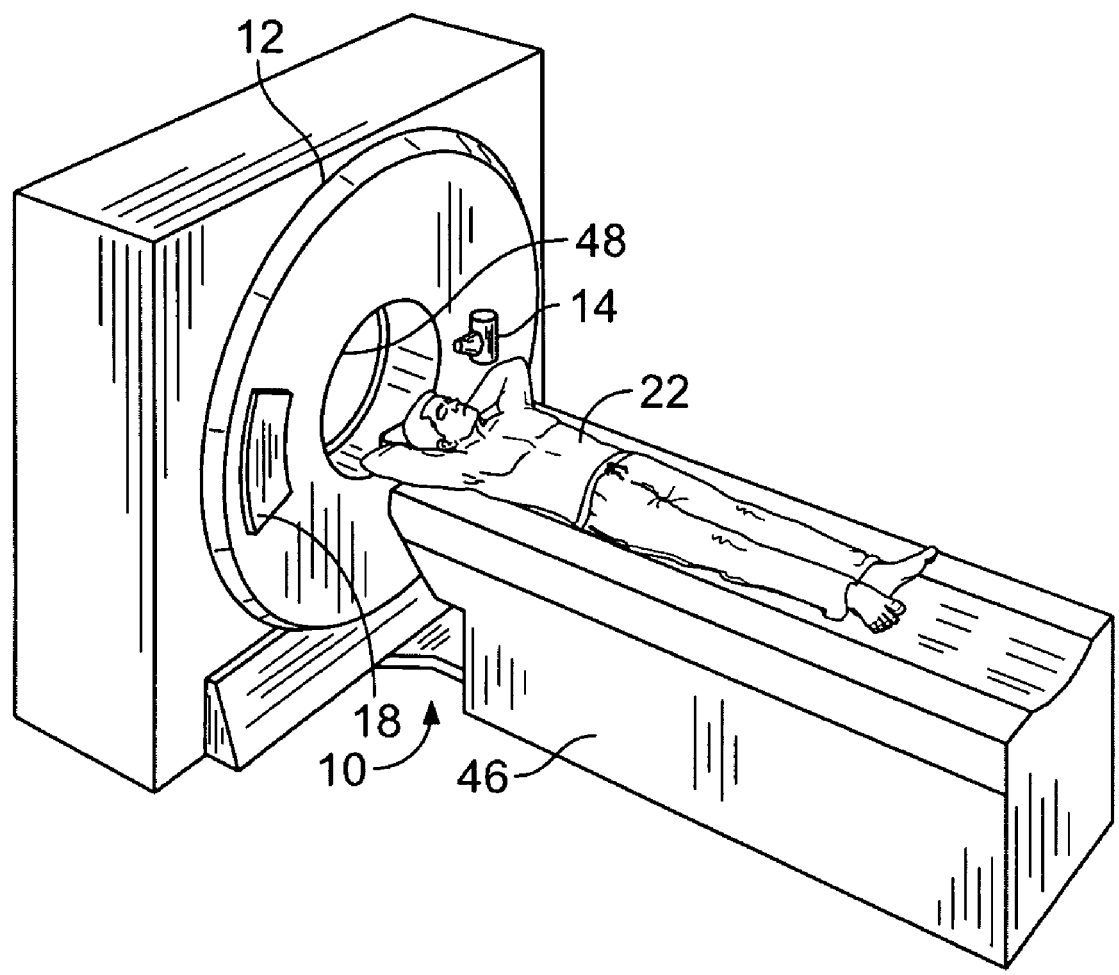
FIG. 1 is a pictorial view of a CT imaging system embodiment.

There are herein provided radiation detection methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the herein described apparatus and methods.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
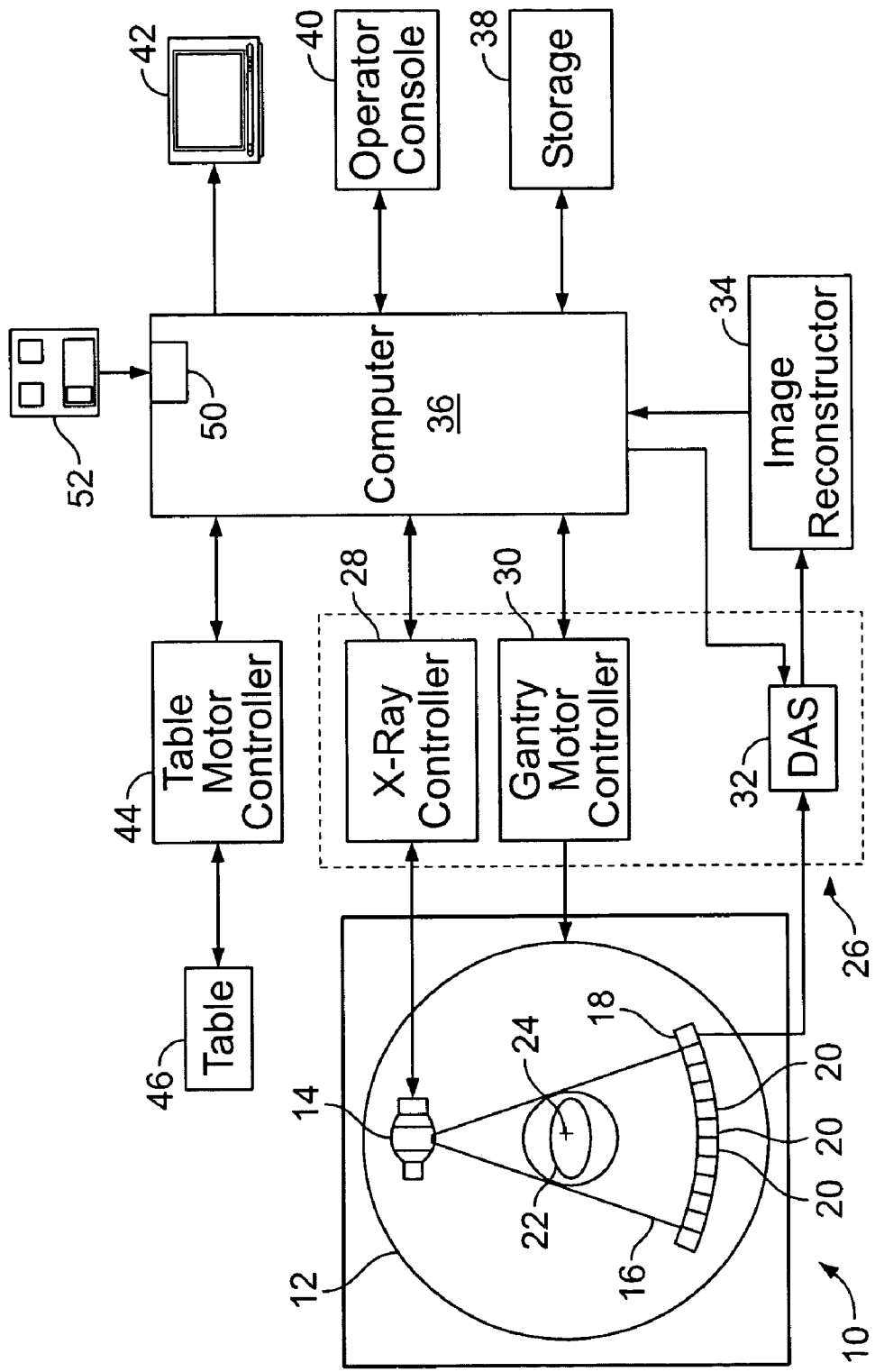
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10 is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

One feature of the herein described methods and apparatus enable a digital module of a CT detector to be field serviced without requiring the replacement of the entire detector. Previously, if an analog module fails, the entire detector is removed and sent back to the factory for repair, which is costly and time consuming. The herein described method and apparatus allow for installation of a digital module for repair and trouble shooting that additionally provides a light seal for the analog module. Furthermore, the card guide facilitates accurate and repeatable installation and removal of the digital module without damaging the sensitive analog portion of the module. In one embodiment, an integrated light seal provides EMI shielding of the low level analog signals produced by the photodiode. Also, in one embodiment, the integrated light seal feature facilitates the prevention of dust and debris from entering the analog region of the detector.

Alternative embodiments are illustrated for locking and retaining the module in place, and for compressing the light seal gasket to ensure a repeatable, reliable, and robust joint. The herein described methods and apparatus enable a low-skilled operation, facilitating field replacement and serviceability of modules.

Figure 3:
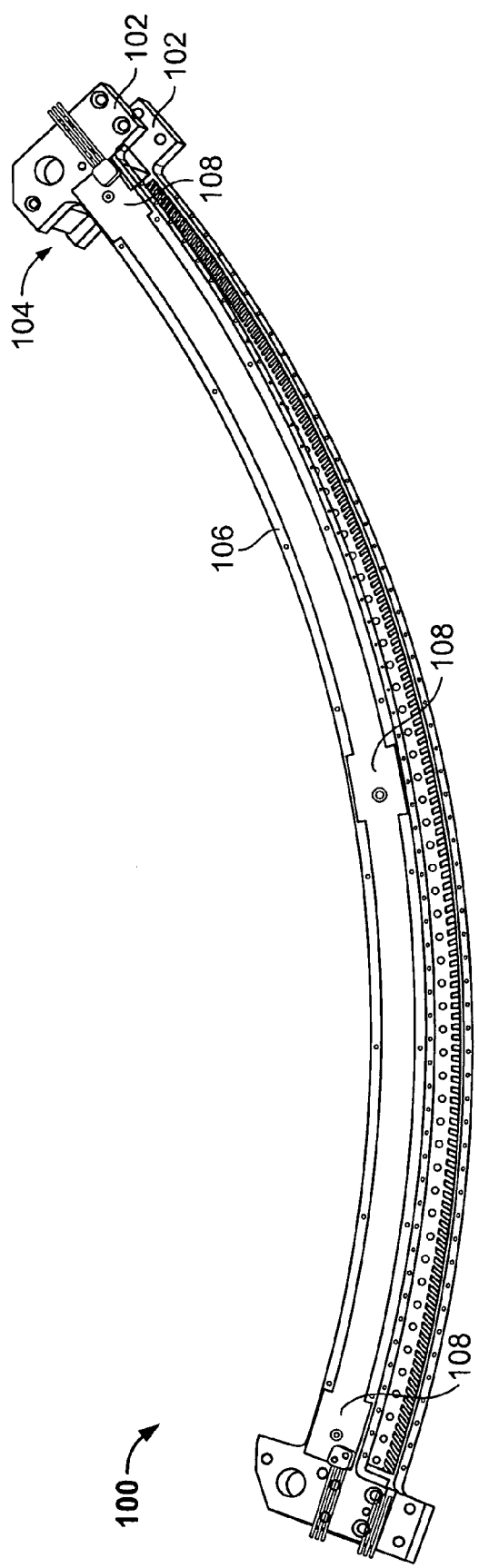
FIG. 3 illustrates a set of rails with a 3 zone heater attached.

FIG. 3 illustrates collimator 100 with rails 102 separated by end blocks 104. Collimator plates (not shown) are mounted and retained between the rails. Three-zone heater 106 is mounted on rail 102, with temperature sensors 108 mounted within rails 102 to control and for feedback control of three-zone heater 106.

Figure 4:
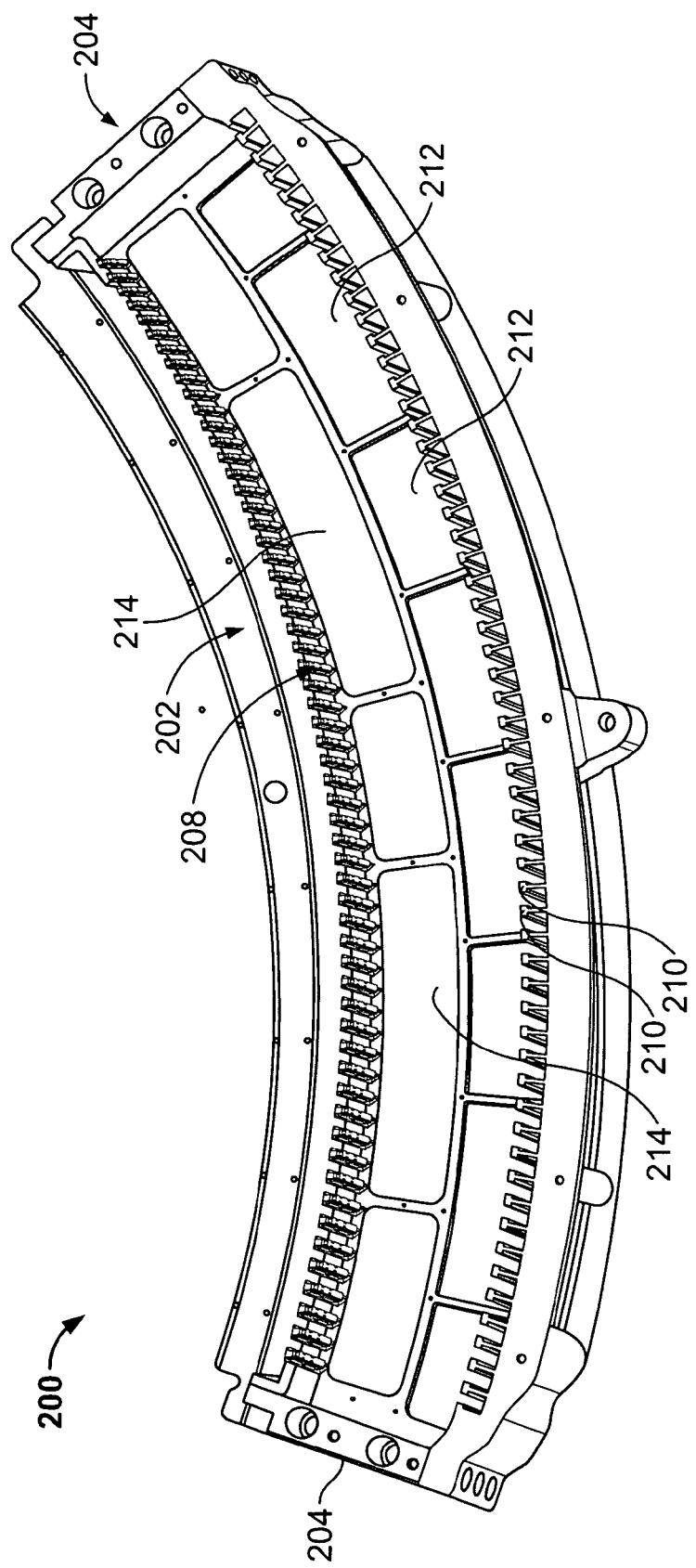
FIG. 4 illustrates a digital module card cage with EMI screen, a back plate, end plates, and card guides.

FIG. 4 illustrates digital module card cage 200. Detector alignment plate 202 with end plates 204 supports card cage 206. Card guides 208 are mounted to detector alignment plate 202, and T-Slots 210 are positioned in card cage 206 and Card guides 208 and T-slots 210 are aligned and pitched one to the other to mount detector modules (not shown). Airways 212 are positioned in detector alignment plate 202 to facilitate air flow over modules when mounted in digital module card cage 200. EMI screen 214 mounts to detector alignment plate 202, positioned to provide EMI protection to modules when mounted in digital module card cage 200.

Figure 5:
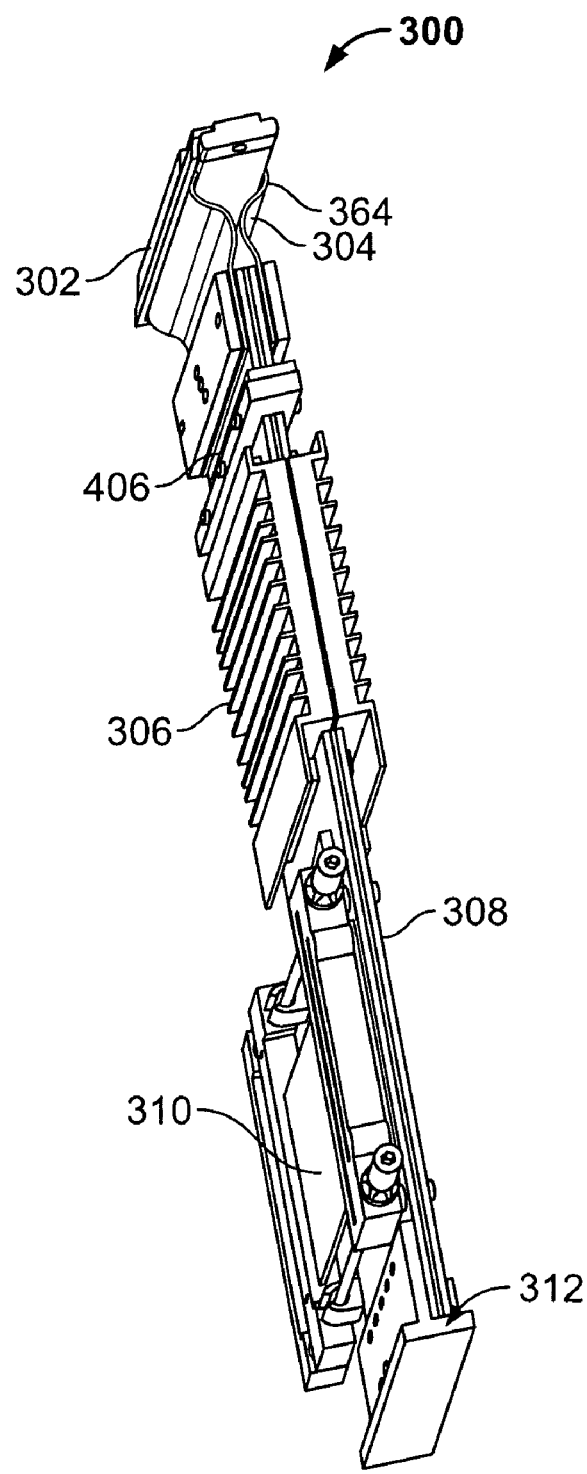
FIG. 5 illustrates a digital module an analog front end, a board guide, heat sink, digital cable, T-slot block, and A/D boards.

FIG. 5 illustrates digital module 300. Analog module 302 converts X-Rays to an analog signal and outputs the signal through flex circuits 304. Analog-Digital (AD) boards 308 convert the analog signals from flex circuits 304 to digital signals using integrated circuits (not shown) positioned under heat sinks 306. Digital signals output through digital cable 310. T-guide 312 is positioned on digital module 300 to engage with T-slot 210 when installed into digital module card cage 200. AD board guide 400 is positioned on digital module 300 to engage card guides 208 when installed into digital module card cage 200.

Figure 6:
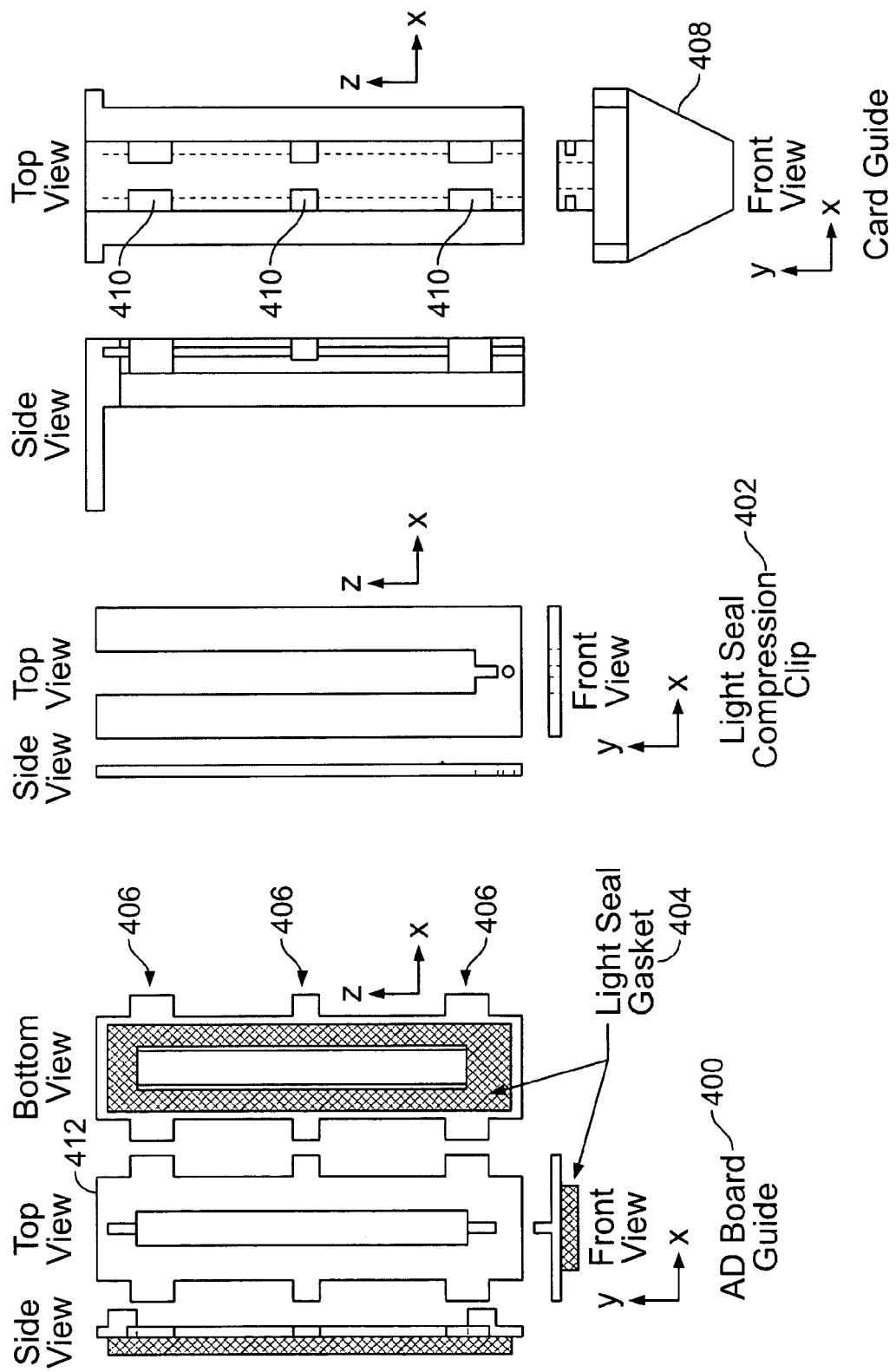
FIG. 6 illustrates a board guide with light seal gasket, a compression clip, and a card guide.

FIG. 6 illustrates AD board guide 400 and light seal compression clip 402. AD board guide 400 has attached light seal gasket 404 onto guide base 412 with guide keys 406. Card guide 408 has key cutouts 410 that mate with guide keys 406 when installed into digital module card cage 200.

Figure 7:
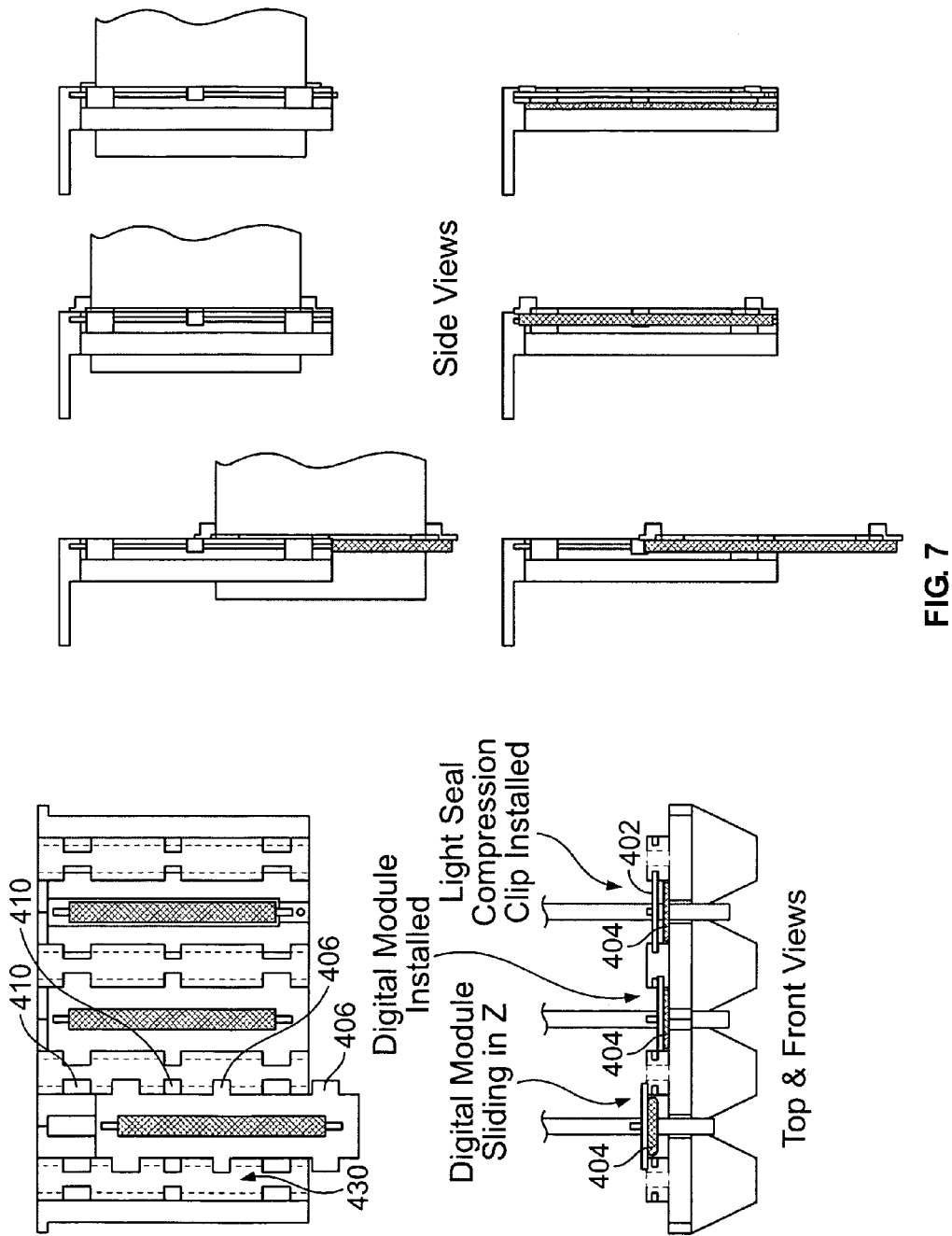
FIG. 7 illustrates module insertion steps and clip installation.

FIG. 7 illustrates three motions for installation of board guide 400, when attached to digital module 300, into card guide 408. Digital module 300 first is moved in direction 430 until guide keys 406 are positioned over key cutouts 410. Once positioned, digital module 300 is engaged by moving in direction 440 and light seal gasket 404 is compressed and light seal compression clip 402 is inserted to retain digital module 300 in card guide 408.

Figure 8C:
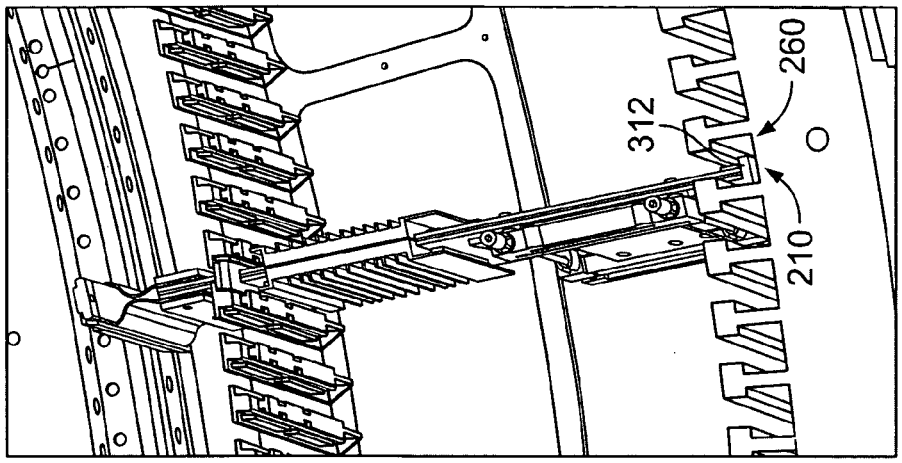
FIG. 8 illustrates digital module positioning in a card guide and a card cage.
Figure 8B:
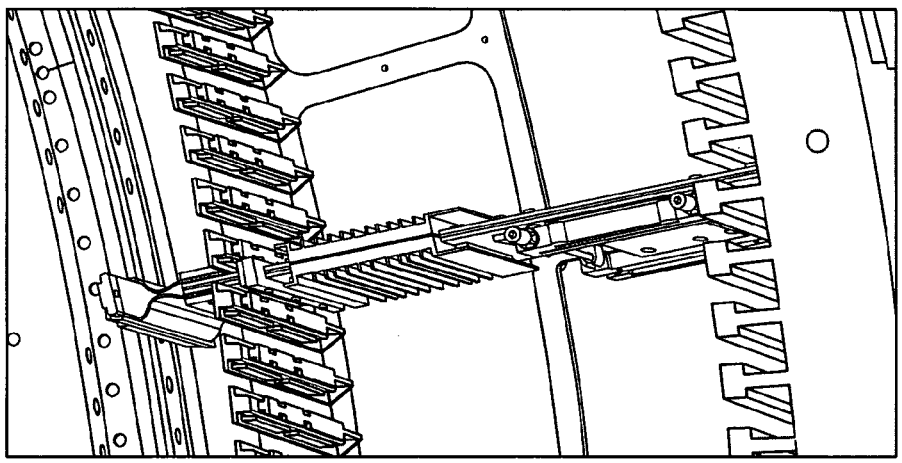
Figure 8A:
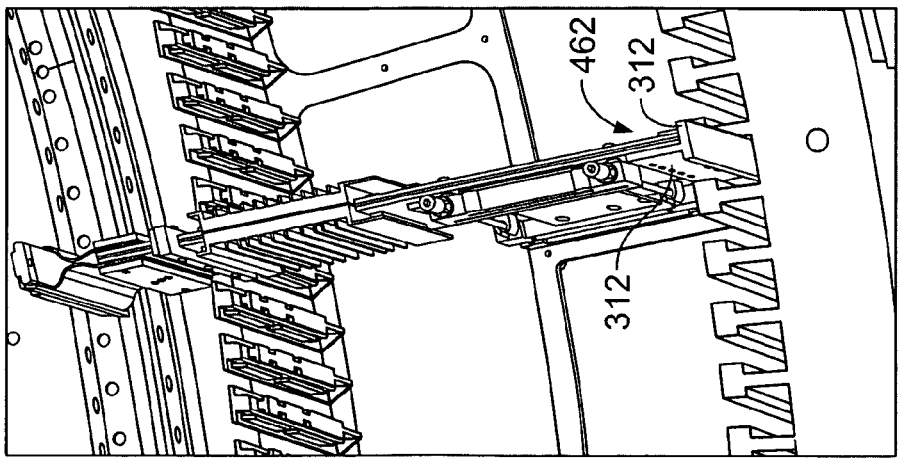

FIG. 8 illustrates a perspective view of the same motion of digital module 300, while also showing the end of digital module 300 with T-guide 312 engaging with T-slot 210. Three steps are illustrated for retaining end portion 462 of digital module 300. View 1 illustrates digital module 300 partially installed in direction 464 while engaging board guide 400 and T-guide 312 during motion in direction 464. View 2 illustrates digital module 300 fully seated in digital module card cage 200. View 3 illustrates wedge clamp 460 frictionally engaged between T-guide 312 and T-slot 210 to retain digital module 300.

Figure 9A:
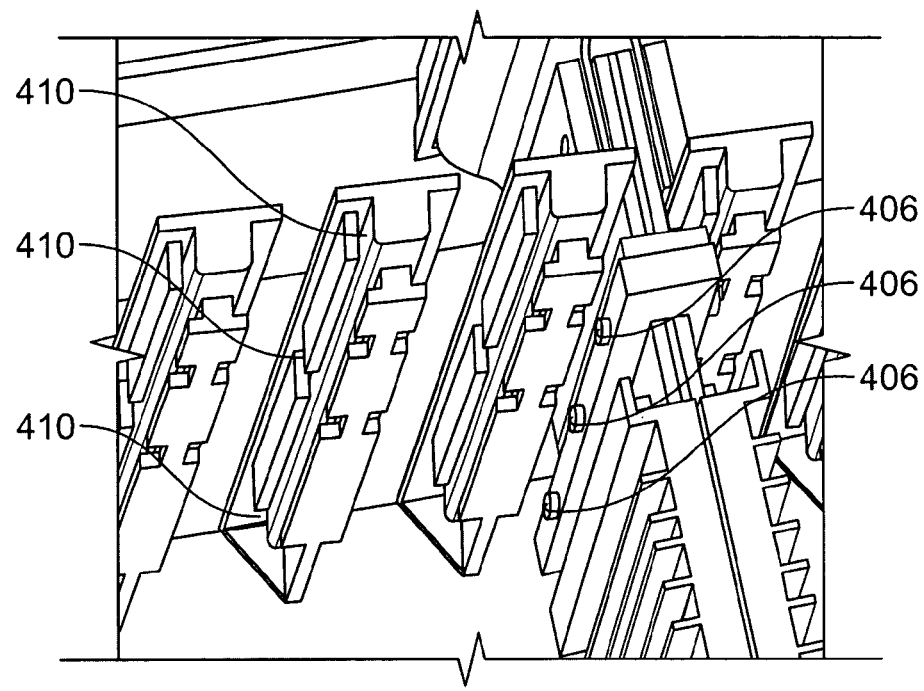
FIG. 9 illustrates digital module positioning and alignment of the front end of the module.
Figure 9B:
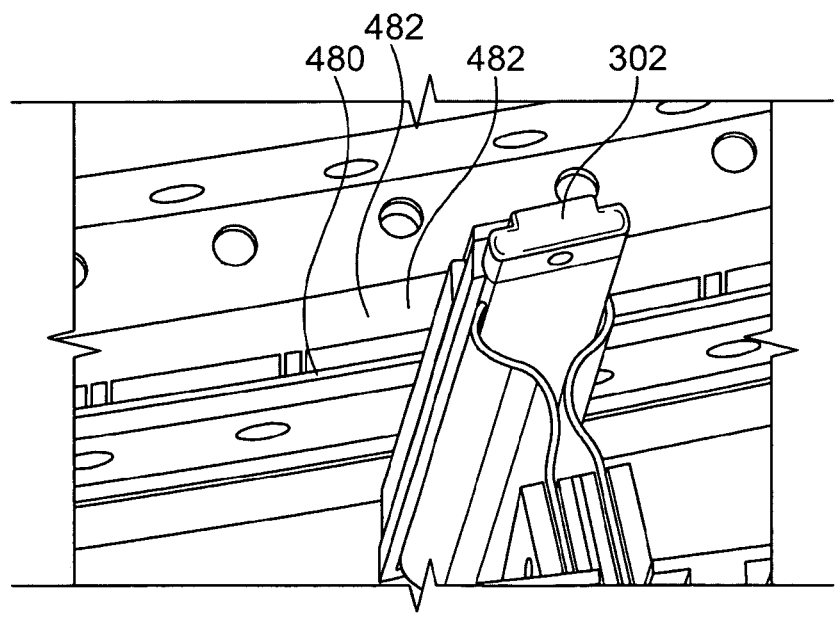

FIG. 9 illustrates engagement of analog module 302 of digital module 300 in collimator 100. Collimator fingers 482 have gaps for positioning of collimator plates (not shown). Alignment fingers 480 extend from selected collimator fingers as illustrated to engage pack alignment pins (not shown) protruding from analog module 302. Once digital module 300 is installed, guide keys 406 engage with key cutouts 410. The card guide alignment features prevent the pack from catching on detector rails until located over alignment pins, and provide rough alignments in X and Z dimensions for analog module 302.

Figure 10:
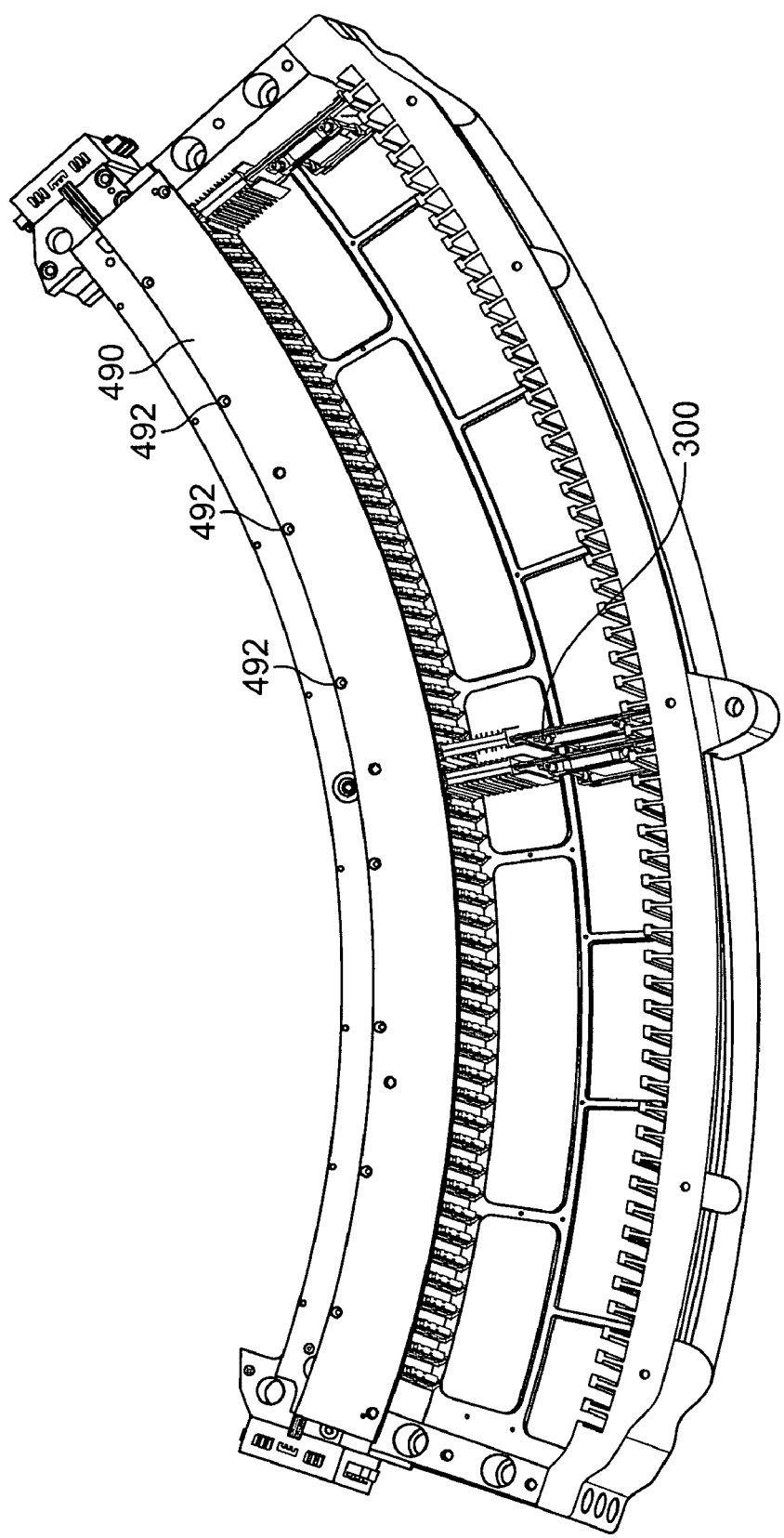
FIG. 10 illustrates a light seal and EMI cover plate positioned over modules after they have been installed into the rails.

FIG. 10 illustrates digital modules 300 installed into digital card cage 200. Light seal cover plate 490 is attached to digital card cage 200 using fasteners 492 to prevent light leakage to analog modules 302 when inserted into digital card cage 200.

Figure 11:
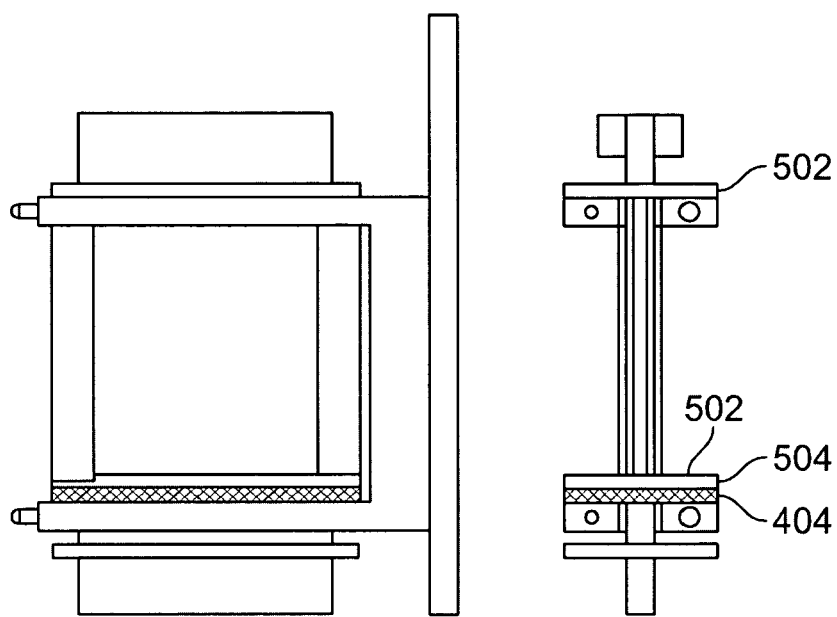
FIG. 11 illustrates a first concept of a card guide with Z motion guides, flow block, and light seal.

FIG. 11 illustrates a first concept for installation of digital module 300 inserted into digital card cage 200. Z motion guide 502 is positioned on digital module 300 to control motion in the Z direction during installation. Flow block 504 is positioned to prevent air flow reaching analog modules 302. Light seal gasket 404 prevents light leakage from reaching analog modules 302.

Figure 12C:
FIG. 12 illustrates a second concept with a master card guide alignment plate and a Wedge Lok clamp.
Figure 12B:
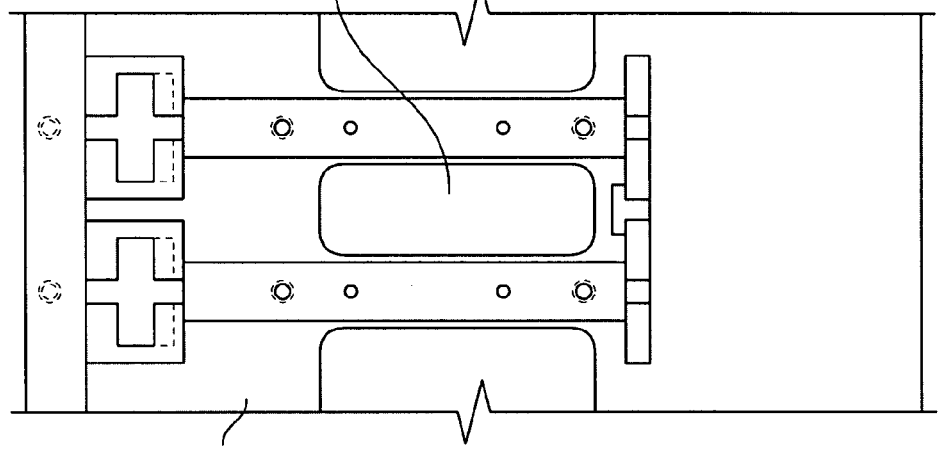
Figure 12A:
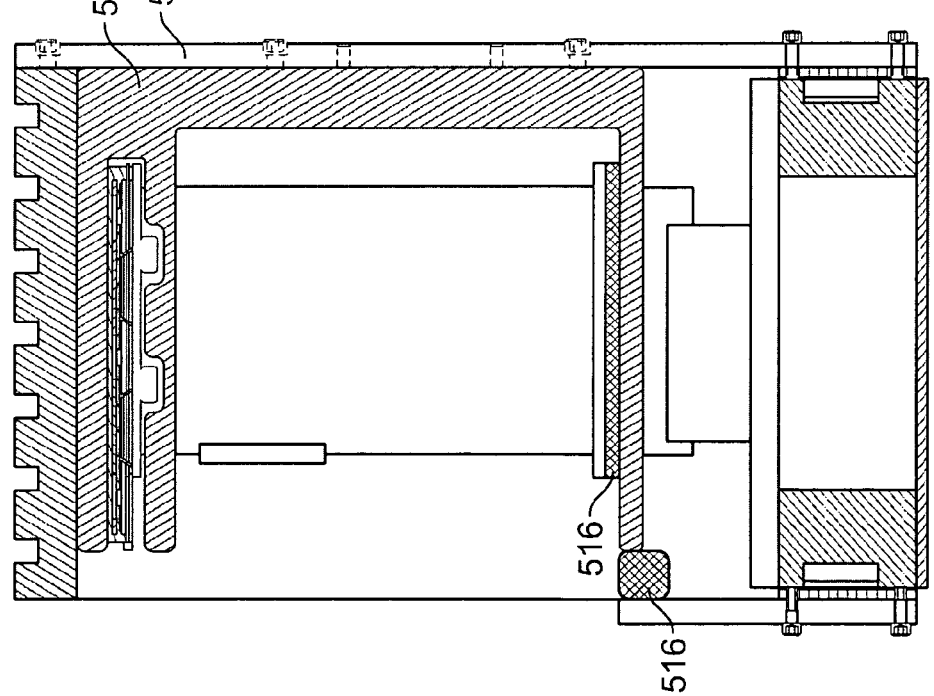

FIG. 12 illustrates a second concept for installation of digital module 300 inserted into digital card cage 200. Master card guide alignment plate 510 has card guide 512 positioned to receive digital modules 300, with air flow cutouts 514 positioned to allow flow over heat sinks 306, with EMI and light seal 516 positioned to protect analog modules 302 from EMI and light exposure. Wedge Lok clamps 518 engage digital modules 300 to retain them during use from motion.

Figure 13:
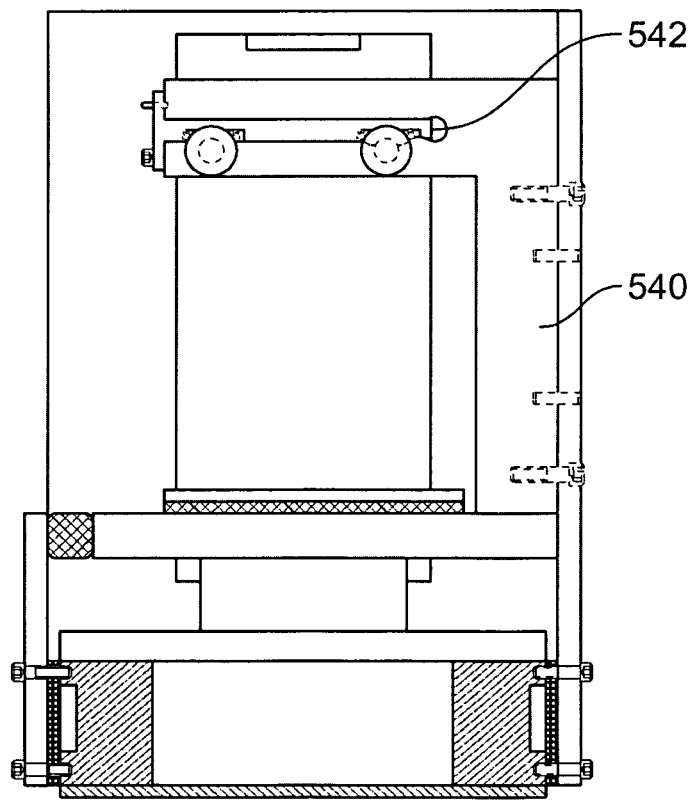
FIG. 13 illustrates a third concept with a top card guide with retention feature for connecting the digital connector.

FIG. 13 illustrates a third concept for installation of digital module 300 inserted into digital card cage 200. Master plate 540 has slot 542 positioned to receive engagement features from digital module 300 to enable alternate designs of digital connector and cable 310. Such design enables simpler connector routing and reduced board length.

Figure 14:
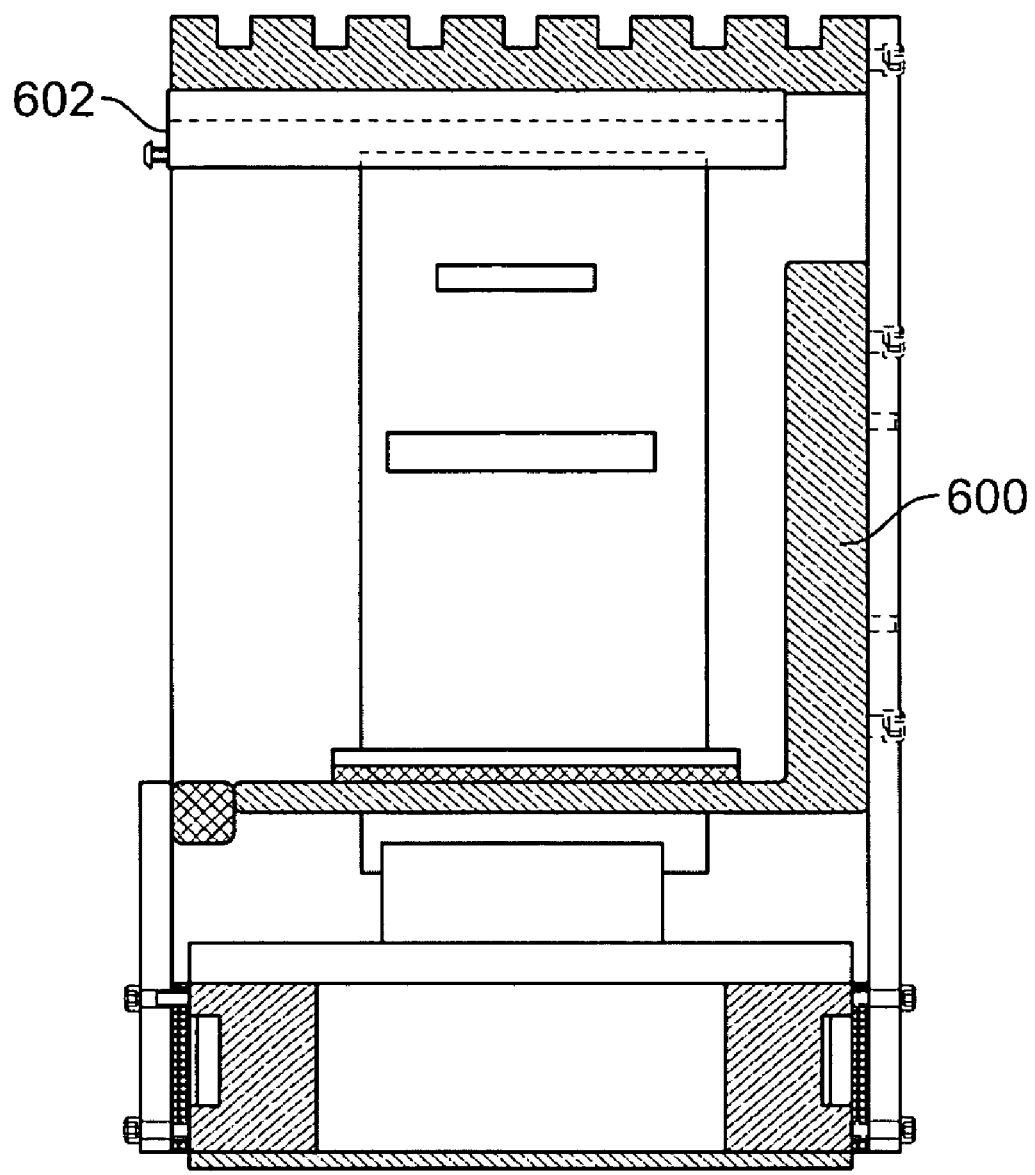
FIG. 14 illustrates a fourth concept with a front seal plate and EMI and light seal with a Wedge Lok clamp.
Figure 15A:
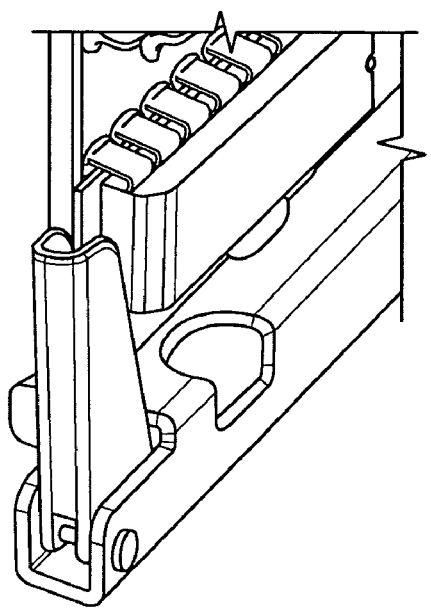
FIG. 15 illustrates a Wedge Lok clamp for use with the digital module.
Figure 15B:
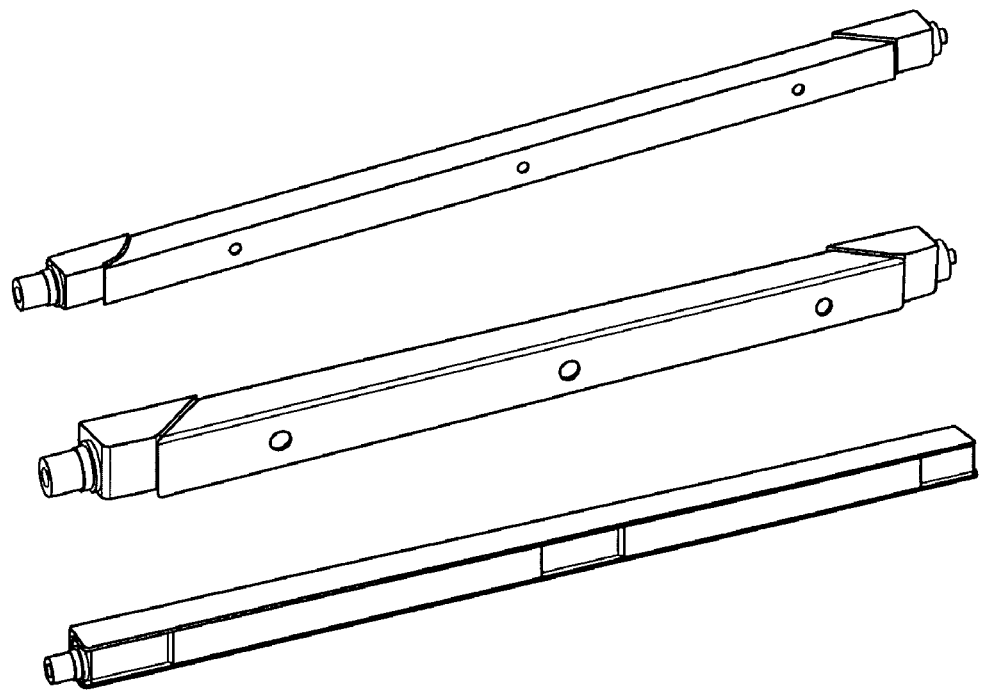
Figure 15C:
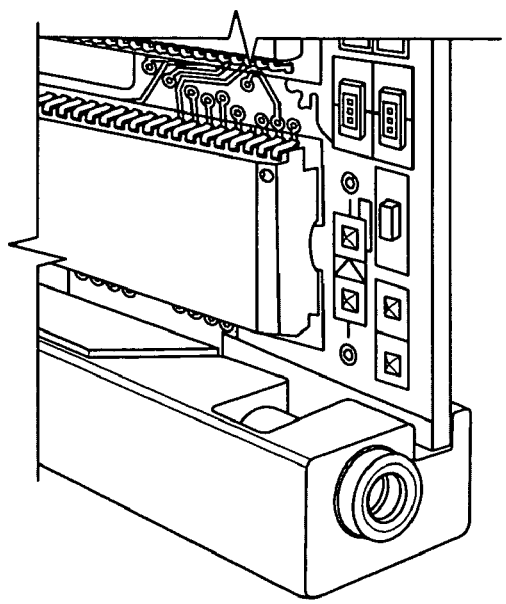
Figure 15D:
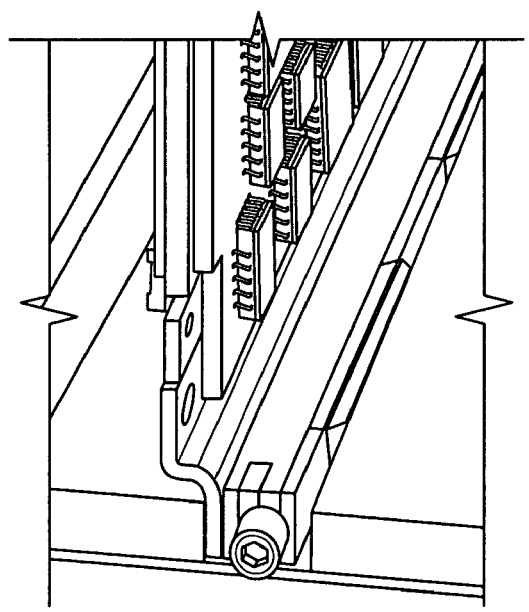
Figure 15E:
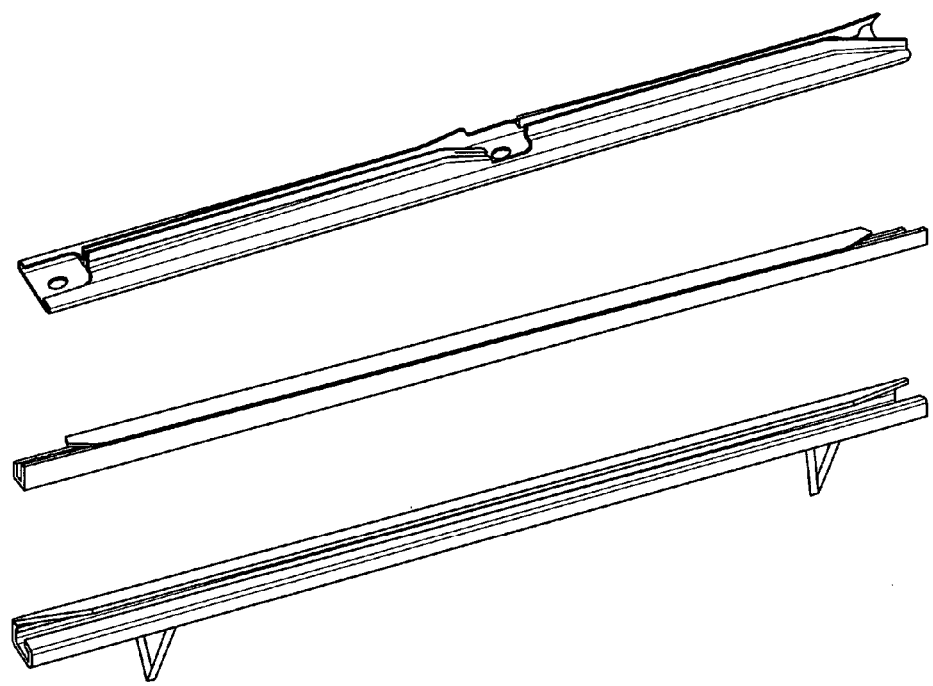

FIG. 14 illustrates a fourth concept for installation of digital module 300 inserted into digital card cage 200. Card guide 600 is positioned to enable wedge clamp 602 to clamp digital module 300.

FIG. 15 illustrates Wedge-Lok card retainers for card retention.

Technical effects of the herein described methods and apparatus provide for a two dimensional card motion control, and a keyed card guide board clip design that provides repeatable and accurate module motion to protect the analog modules and collimator from damage. Additional technical effects include the field replaceability of an integrated analog and digital DAS assembly, the repeatable lights sealing of an analog module, and for digital module locking and retaining that automatically crushes light seal gaskets to ensure light seal. Other technical effects are an integrated accessory clip that automatically crushes light seal gaskets to ensure light seal, and a light seal design that also performs dust and EMI shielding of the collimator and analog module.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method of installing an electronic board comprising:
    inserting the electronic board into a guide in a first direction;

translating the electronic board in a second direction, sealing a gasket to facilitate preventing light, dust and electromagnetic interference (EMI) from passing the gasket;

engaging a first lock such that the electronic board is maintained in a substantially fixed position; and engaging a second lock to prevent movement of the electronic board in the reverse of the second direction, the second lock further including a wedge lock, wherein the wedge lock includes an insertion portion having slots and a tubular portion having tabs, such that the tabs lock into the slots upon rotation of the tubular portion.

2. A method in accordance with claim 1 wherein the first direction is different than the second direction.

3. A method in accordance with claim 1 wherein the first direction and second direction are orthogonal with respect to each other.

4. A method in accordance with claim 1 further comprising restricting movement of the electronic board during translation to a predetermined path to facilitate preventing adjacent components from being contacted during translation of the electronic board.

5. A method in accordance with claim 1 wherein inserting a second lock further comprises inserting a wedge clamp.

6. A method in accordance with claim 1 wherein engaging a second lock further comprises positioning an engagement feature into a slot.

7. An electronic board assembly comprising:
a guide configured to receive said electronic board in a first direction and a second direction;
a gasket, said gasket sealed when said electronic board is inserted into said guide in said second direction such that light, dust and electromagnetic interference (EMI) are prevented from passing said gasket;
a first lock configured to maintain said electronic board in a substantially fixed position; and
a second lock to prevent movement of said board in the reverse of said second direction said second lock further comprising a wedge lock, wherein said wedge lock comprises an insertion portion having slots and tubular portion having tabs, such that said tabs lock into said slots upon rotation of said tubular portion.

8. An electronic board in accordance with claim 7 wherein said electronic board further comprises an analog module and a flow block, said flow block positioned to prevent air flow from reaching said analog module.

9. An electronic board in accordance with claim 7 wherein said second lock further comprises a wedge clamp.

10. An electronic board in accordance with claim 7 wherein said second lock further comprises a slot and an engagement feature, said engagement feature complimentary to said slots.

11. A medical system comprising:
a guide; and
an electronic board configured to be received into said guide in a first and second direction, said electronic board further comprising:
a gasket, said gasket sealed when said electronic board is inserted into said guide in said second direction such that light, dust and electromagnetic interference (EMI) are prevented from passing said gasket;
a first lock to maintain said electronic board in a substantially fixed position; and
a second lock to prevent movement of said board in the reverse of said second direction said second lock further comprising a wedge lock, wherein said wedge lock comprises an insertion portion having slots and tubular portion having tabs, such that said tabs lock into said slots upon rotation of said tubular portion.

12. A medical system in accordance with claim 11 wherein said guide further comprises a predetermined path to facilitate preventing adjacent components from being contacted during installation of said electronic board.

13. A medical system in accordance with claim 11 wherein said second lock further comprises a wedge clamp.

14. A medical system in accordance with claim 11 wherein said second lock further comprises a slot and an engagement feature, said engagement feature configured to be complimentary to said slots.

* * * * *